(12) United States Patent
De Haan et al.

(10) Patent No.: US 10,683,520 B2
(45) Date of Patent: *Jun. 16, 2020

(54) POLYCARBOXYLIC ACID EXTRACTION

(71) Applicant: PURAC BIOCHEM BV, Gorinchem (NL)

(72) Inventors: André Banier De Haan, Best (NL); Jan Van Krieken, Gorinchem (NL); Tanja Đekic Živkovic, 's-Hertogenbosch (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,620

(22) PCT Filed: Dec. 21, 2012

(86) PCT No.: PCT/EP2012/076735
§ 371 (c)(1),
(2) Date: Jun. 18, 2014

(87) PCT Pub. No.: WO2013/093043
PCT Pub. Date: Jun. 27, 2013

(65) Prior Publication Data
US 2014/0349355 A1 Nov. 27, 2014

Related U.S. Application Data

(60) Provisional application No. 61/579,730, filed on Dec. 23, 2011.

(30) Foreign Application Priority Data

Dec. 23, 2011 (EP) ..................... 11195691

(51) Int. Cl.
C07C 51/50 (2006.01)
C12P 7/44 (2006.01)
C07C 51/48 (2006.01)
C12P 7/46 (2006.01)

(52) U.S. Cl.
CPC ............ *C12P 7/44* (2013.01); *C07C 51/48* (2013.01); *C12P 7/46* (2013.01)

(58) Field of Classification Search
CPC ......... C07C 51/48; C07C 57/13; C07C 29/86; C07C 227/40; C07C 229/24; C07C 55/10; C07C 55/14; C07C 59/08; C07C 59/265; C12P 7/44; C12P 7/46
USPC ......................................... 435/142; 562/593
IPC ............... C12P 7/44; B01D 11/04; C02F 1/44
See application file for complete search history.

(56) References Cited

U.S. PATENT DOCUMENTS

| | | | | |
|---|---|---|---|---|
| 2,710,880 A | * | 6/1955 | Filachione | C07C 51/48 562/580 |
| 3,786,096 A | | 1/1974 | Konno | |
| 4,275,234 A | | 6/1981 | Baniel et al. | |
| 4,698,303 A | * | 10/1987 | Bailey | A23C 21/023 426/43 |
| 5,426,219 A | | 6/1995 | Lehnhardt et al. | |
| 6,229,046 B1 | * | 5/2001 | Eyal | C07C 51/48 562/589 |
| 8,062,871 B2 | * | 11/2011 | Burgard | C12P 7/44 435/135 |
| 9,422,217 B2 | | 8/2016 | Kon et al. | |
| 2001/0014758 A1 | * | 8/2001 | Baniel | C12P 7/56 562/580 |
| 2007/0193960 A1 | * | 8/2007 | Frank | C07C 29/86 210/806 |

FOREIGN PATENT DOCUMENTS

| | | |
|---|---|---|
| CN | 101 979 368 A | 2/2011 |
| CN | 102 690 189 A | 9/2012 |
| GB | 173 479 A | 11/1922 |
| GB | 280 969 A | 6/1928 |
| JP | A-08-337552 | 12/1996 |
| JP | H09-500649 A | 1/1997 |
| WO | 94/19307 A1 | 9/1994 |
| WO | WO 95/03268 A1 | 2/1995 |

(Continued)

OTHER PUBLICATIONS

Koopman et al. 2010. Efficient whole-cell biotransformation of 5-hydroxymethyl) furfural into FDCA, 2, 5-furandicarboxylic acid. Bioresource Technology, vol. 101:6291-6296.*
Dow Chemical Company 2002 MIBK Technical Data sheet downlod printed Sep. 30, 2017, 2002.*
Britannica. (Lactic acid No date specified, printedSep. 30, 2017, No date.*
Hydrochloric acid: Physical and Chemical Properties, https://psa-hydrochloric-acid.weebly.com/physical--chemical-properties.html, 2 pages accessed Feb. 22, 2018 (Year: 2018).*

(Continued)

*Primary Examiner* — Thane Underdahl
(74) *Attorney, Agent, or Firm* — Oliff PLC

(57) ABSTRACT

The invention pertains to method for recovering polycarboxylic acid from an aqueous mixture including the steps of: providing an aqueous mixture including polycarboxylic acid and at least 5 wt. % dissolved halide salt, based on the total weight of water and dissolved material in the aqueous mixture; extracting the polycarboxylic acid from the aqueous mixture into a first organic liquid including an organic solvent selected from the group consisting of ketones and ethers, thereby obtaining an organic polycarboxylic acid solution and an aqueous waste liquid including the halide salt; and extracting the polycarboxylic acid from the organic carboxylic acid solution into an aqueous liquid, thereby obtaining an aqueous polycarboxylic acid solution and a second organic liquid. The method according to the invention allows a combined purification and concentration step for feed solutions of polycarboxylic acids.

27 Claims, 1 Drawing Sheet

(56) References Cited

FOREIGN PATENT DOCUMENTS

WO　　WO 00/17378 A2　　3/2000

OTHER PUBLICATIONS

PubChem "Methyl Ethyl Ketone" 4 pgs, accessed Feb. 22, 2018 (Year: 2018).*
Apr. 16, 2013 International Search Report issued in International Patent Application No. PCT/EP2012/076735.
Apr. 16, 2013 Written Opinion issued in International Patent Application No. PCT/EP2012/076735.
Substantial, Definition of Substantial by Merriam-Webster, May 21, 2016, 1 page, http://www.merriam-webster.com/dictionary/substantial.
G. Jurriens et al., "Analysis of Calcium Salts of Fatty Acid-Lactic Acid Condensates," Calcium Salts of Acid Condensates, vol. 43, Nov. 1966, pp. 669-674.
Jun. 30, 2016 Office Action issued in U.S. Appl. No. 14/366,595.
Aug. 18, 2015 Office Action Issued in Korean Patent Application No. 10-2014-7020313.
Wasewar et al., "Equilibrium Study for Reactive Extraction of Caproic Acid in Mibk and Xylene," Department of Chemical Engineering Visvesvaraya National Insitute of Technology, vol. 3, pp. 829-835 (2001).
Goswami et al., "Fed-batch propionic acid production by Propionibacterium acidipropionici," Biomedical Engineering Journal, vol. 4, pp. 121-128 (2000).
Apr. 8, 2013 International Search Report issued in International Patent Application No. PCT/EP201/076696.
Apr. 8, 2013 Written Opinion issued in International Patent Application No. PCT/EP2012/076696.
Mar. 27, 2013 Written Opinion issued in International Patent Application No. PCT/EP2012/076741.
Mar. 27, 2013 International Search Report issued in International Patent Application No. PCT/EP2012/076741.
Nov. 11, 2015 Office Action issued in Japanese Patent Application No. 2014-548085.
Nov. 11, 2015 Office Action issued in Japanese Patent Application No. 2014-548084.
Nov. 10, 2015 Office Action issued in Japanese Patent Application No. 2014-548079.
U.S. Appl. No. 14/366,628, filed Jun. 18, 2014 in the name of De Haan et al.
U.S. Appl. No. 14/366,595, filed Jun. 18, 2014 in the name of De Haan et al.
Oct. 15, 2015 Election of Species Requirement issued in U.S. Appl. No. 14/366,628.
Feb. 2, 2016 Office Action issued in U.S. Appl. No. 14/366,628.
Oct. 21, 2015 Office Action issued in U.S. Appl. No. 14/366,595.
May 4, 2017 U.S. Office Action Issued in U.S. Appl. No. 14/366,595.
Oct. 13, 2016 Office Action Issued in U.S. Appl. No. 14/366,628.
Doi et al. 1988. Nuclear Magnetic Resonance Studies on Unusual Bacterial Copolyesters of 3-Hyroxybutyrate and 4-Hydroxybutyrate. Macromolecules, vol. 21:2722-2727.
Oct. 4, 2017 Office Action Issued in U.S. Appl. No. 14/366,628. 10 pgs.
Jan. 11, 2018 Office Action issued in Indian Application No. 5067/CHENP/2014.
Mar. 7, 2019 Office Action Issued in U.S. Appl. No. 14/366,628.
Dec. 12, 2019 Office Action issued in U.S. Appl. No. 14/366,628.
Apr. 1, 2016 Office Action issued in Korean Patent Application No. 10-2014-7020313.
Jun. 1, 2016 Office Action issued in Vietnamese Patent Application No. 1-2014-02254.
Apr. 28, 2016 Office Action issued in Ukranian Patent Application No. a 2014 07598.

\* cited by examiner

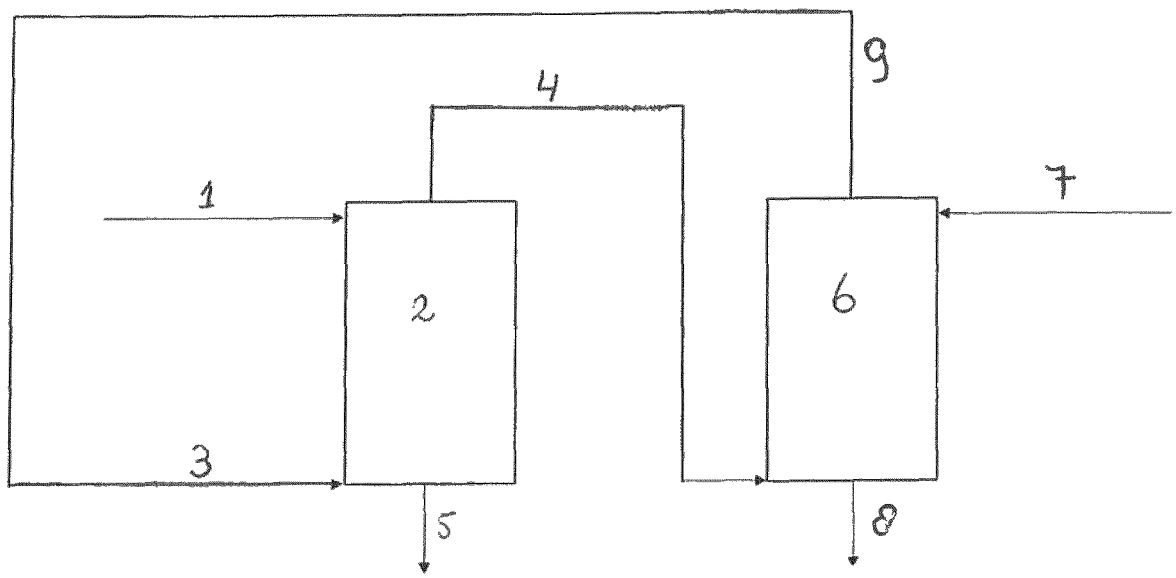

POLYCARBOXYLIC ACID EXTRACTION

RELATED APPLICATIONS

This application is a National Phase of International Application No. PCT/EP2012/076735 filed on Dec. 21, 2002, which claims priority to U.S. Provisional Patent Application No. 61/579,730 filed on Dec. 23, 2011 and European Application No. 11195691.8.

The invention is directed to a method for preparing a polycarboxylic acid solution using extraction.

Isolating carboxylic acids from an aqueous mixture comprising impurities such as salts can be difficult. Carboxylic acids, can be manufactured via fermentation of a carbon source, such as carbohydrates or glycerol, by micro-organisms. In such a fermentation process a carbohydrate source is typically fermented by means of a micro-organism to form a carboxylic acid. The liquid wherein the carbohydrate source is fermented is called the fermentation broth or the fermentation medium. The formation of carboxylic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH. As a result, carboxylic acid produced in the fermentation media is typically present in the form of a carboxylate salt. Although there are micro-organisms that are to some extent resistant to acidic environments, such that fermentation can be conducted at a low pH (e.g. at a pH of 3), even in these processes at least part of the carboxylic acid is obtained as a carboxylate salt.

To recover the carboxylic acid from the fermentation broth after fermentation, downstream processing is required. In such processing, the carboxylate salt in the fermentation broth needs to be converted into carboxylic acid. Also, the carboxylic acid (or carboxylate if not yet converted) needs to be isolated from the fermentation broth. Since a fermentation broth comprises many compounds, including significant amounts of biomass (such as micro-organisms) and salt (originating from the neutralizing agent), recovering and isolating carboxylic acid can be rather complex, typically requiring multiple processing steps and leading to waste material, in particular salt waste.

For polycarboxylic acids, specific problems occur. Polyacids generally have a low solubility in water. One the one hand this means that the major body of polyacids can be removed from water relatively easily using methods like precipitation or crystallisation. On the other hand, this results in the formation of dilute acid solutions from which for economic reasons and for HSE reasons it is still desired to remove the polyacid. While it is possible to remove the last fractions also by crystallisation or precipitation this involves multiple stage operation which requires expensive apparatus and operating conditions. There is therefore need for a method for removing polycarboxylic acids from aqueous solutions which combines efficient removal with relatively low-cost operation.

WO95/03268 describes a process for recovering an organic acid, including mono-, di-, and tricarboxylic acids comprised of 3-8 carbon atoms from a fermentation broth by clarifying the broth to remove at least a substantial portion of the impurities therein, producing a clarified feed; acidulating the clarified feed by adding a quantity of a mineral acid effective to lower the pH of the feed to between about 1.0 and about 4.5, producing an acidulated feed which is substantially saturated with respect to at least one electrolyte selected from the group consisting of MHSO4, M2SO4, M3PO4, M2HPO4, MH2PO4, and MNO3, where M is selected from the group consisting of Na, NH4, and K; extracting the acidulated feed with an extraction mixture which includes (a) water, (b) a mineral acid, in a quantity effective to maintain the pH of the feed between about 1.0 and about 4.5, and (c) an oxygenated solvent which has limited miscibility with water. The extraction produces a solvent extract and a first raffinate. The solvent extract is subjected to back-extraction with an aqueous liquid, thereby producing an organic acid-rich aqueous extract and an organic acid-depleted solvent raffinate.

A problem with the sequence of extraction followed by back extraction is the formation of dilute liquids. Generally, when a compound is extracted from water using an organic liquid, and subsequently extracted from the organic liquid using water, the concentration of the compound in the product aqueous liquid is lower than that in the starting aqueous liquid. This is of course disadvantageous, because it generates dilute liquids which require further concentration. This is of particular importance where the starting liquid already has a relatively low acid concentration, as in the case of the relatively insoluble polyacids. There is therefore need in the art for an extraction/back extraction process for polycarboxylic acids, which allows the isolation of a polycarboxylic acid from a salt solution, even where the concentration of polyacid is relatively low, without the formation of more dilute acid solutions. The present invention provides such a process.

The present invention is directed to a method for recovering polycarboxylic acid from an aqueous mixture comprising the steps of providing an aqueous mixture comprising polycarboxylic acid and at least 5 wt. % dissolved halide salt, based on the total weight of water and dissolved material in the aqueous mixture, extracting the polycarboxylic acid from the aqueous mixture into a first organic liquid comprising an organic solvent selected from the group consisting of ketones and ethers, thereby obtaining an organic polycarboxylic acid solution and an aqueous waste liquid comprising the halide salt, and extracting the polycarboxylic acid from the organic carboxylic acid solution into an aqueous liquid, thereby obtaining an aqueous polycarboxylic acid solution and a second organic liquid.

It is noted that CN101979368 describes extraction of acid from a solution containing a salt. The extractant is methanol, ethanol, n-propanol, isopropanol, n-butanol, isobutanol, acetone, ethylene glycol, diethyl ether, methyl acetate or ethyl acetate.

JP8-337552 describes conversion of an acid salt to acid, followed by extraction takes place with an oxygenated saturated heterocycle type solvent.

Neither reference discloses a back extraction process. Therefore, these references are not relevant.

It was found that the process according to the invention, which is characterised by the use of a specific carboxylic acid, namely a polycarboxylic acid, in combination with a specific salt, namely a halide salt, in a specific amount, namely in an amount of at least 5 wt. % dissolved halide salt, leads to a process wherein the concentration of the carboxylic acid in the aqueous solution obtained after forward extraction and back extraction is higher than in the aqueous mixture before extraction. This concentration effect is for example advantageous when the aqueous carboxylic acid solution obtained after back extraction is to be concentrated, in which case energy costs are saved by having to evaporate less water to obtain a certain carboxylic acid concentration. Further, the product obtained in the process according to the invention has high purity. Other advantages of the present invention will become apparent from the further specification.

Not wishing to be bound by theory, it is believed that one or more of the following effects may occur in the extraction process according to the invention.

It may be that the presence of the halide salt in the aqueous mixture enhances the extraction of the carboxylic acid from the aqueous mixture into the first organic liquid. This will contribute to the concentration effect described above. Second, it may be that the dissolved halide salt decreases the solubility of the organic solvent in water. In particular, at higher concentrations of dissolved halide salt, less ketone-based solvent (such as for example MIBK) might dissolve in the aqueous mixture. This effect may be stronger at higher temperatures, in particular in the temperature range of 20° to 100° C. Accordingly, forward and/or back extraction are preferably conducted at a temperature of at least 25° C., preferably at least 30° C., more preferably at least 40° C. It is contemplated that this effect holds true for ketones and ethers in general. The lower solubility of the organic liquid in water will result in streams with higher purity and less solvent losses in both the forward and back extraction and may thus lead to a more efficient process. In contrast, the solubility of water in alcohol and the solubility of alcohol in water increases when increasing the temperature in temperature range of 25° C. and 100° C.

Third, the solubility of the water in the organic solvent during extraction may also be decreased by the presence of the dissolved halide salt.

Fourth, it was found that dissolved halide salt may suppress emulsion formation, thereby enhancing phase-separation between the aqueous and organic liquids. This is in particular advantageous when the aqueous mixture comprises traces of biomass. Biomass originating from a fermentation process typically comprises compounds that can act as surfactants. Consequently, when an aqueous mixture comprising biomass is brought into contact with an organic solvent, typically an emulsion will be formed. Such emulsion formation is undesirable, because it may disrupt the extraction process and phase separation.

Further preferred embodiments of the present invention will be described below.

FIG. 1 gives a schematic representation of the an embodiment of the present invention. In FIG. 1, (1) is the aqueous starting mixture, which, where it is provided to an extraction reactor (2), where it is contacted with organic liquid (3). A stream (4), which comprises carboxylic acid in the organic liquid is withdrawn from the extraction reactor (2). Aqueous waste liquid (5) is also withdrawn from extraction reactor (2). Stream (4) comprising carboxylic acid in the organic liquid is provided to back-extraction reactor (6), where it is contacted with aqueous liquid provided through line (7). The product aqueous carboxylic acid solution is withdrawn through line (8). The organic liquid is withdrawn through line (9), and recycled to the extraction reactor (2) through line (3), optionally after intermediate purification steps (not shown).

The term "extraction" as used herein refers to liquid-liquid extraction, also known as solvent extraction. Solvent extraction is an extraction method based on the difference in solubility of a compound in two different liquids, i.e. in the present case the solubility of the carboxylic acid in water (present in the aqueous mixture and the aqueous liquid) relative to the solubility of the carboxylic acid in the organic solvent (present in the organic liquid). Forward extraction is the process wherein the compound to be extracted is extracted from the aqueous mixture into the organic liquid. Back extraction is the process wherein the compound to be extracted is extracted from the organic liquid into an aqueous liquid.

The term "solubility" as used herein refers to the maximum weight amount of a compound that can be dissolved in a certain amount of an aqueous mixture at a certain temperature.

Forward extraction and back extraction as used in the method of the invention are based on the difference in solubility of the carboxylic acid in water and the organic solvent at different temperatures. The solubility of a compound in one solvent relative to another solvent can be expressed in terms of the distribution ratio (DR). This ratio gives an indication how a compound will be distributed over the aqueous phase (e.g. the aqueous mixture) and the organic phase (e.g. the organic liquid) in a two-phase system at equilibrium. The distribution ratio may be defined as the ratio of the carboxylic acid concentration dissolved in the organic phase ([carboxylic acid]$_{organic}$) over the concentration of the carboxylic acid dissolved in water ([carboxylic acid]$_{water}$), provided that the two phases are in equilibrium with each other:

$$DR=[\text{carboxylic acid}]_{organic}/[\text{carboxylic acid}]_{water} \quad (1)$$

From formula (1) it can be concluded that the higher the distribution ratio, the more carboxylic acid will dissolve in the organic phase.

The distribution ratio depends on many variables, including the temperature and the specific composition of the organic and water phase. For example, the concentration of the dissolved halide salt in the aqueous mixture and the type of solvent used will influence the distribution ratio.

During forward extraction, the carboxylic acid should preferably dissolve better in the organic solvent than in water. Consequently, the distribution ratio in the forward extraction should be as high as possible. In particular, a high distribution ratio during forward extraction is desirable as any carboxylic acid still present in the waste liquid will directly lead to a decrease of the total carboxylic acid yield when this waste liquid cannot be reworked and/or recycled back to the process again, or used for other purposes and should be disposed off. In case the distribution ratio during forward extraction is high, relatively little carboxylic acid will be lost since most of the carboxylic acid will have been dissolved in the organic liquid. It is preferred for the DR in forward extraction, also indicated as $D_{FE}$ to be at least 0.1, more in particular at least 0.4, still more in particular at least 0.8.

During back extraction, the opposite holds true. The carboxylic acid should preferably dissolve better in the aqueous phase than in the organic liquid. It is preferred for the DR in the backward extraction, also indicated as also indicated as $D_{BE}$ to be at most 0.5, more in particular at most 0.3, still more in particular at most 0.1.

If the distribution ratio for forward extraction is higher than the distribution ratio for back extraction, this will contribute to a concentration effect, wherein the aqueous carboxylic acid solution obtained after back extraction has a higher concentration of carboxylic acid than the aqueous mixture used as starting material in the forward extraction. It is preferred for the ratio between $D_{FE}$ and $D_{BE}$ to be at least at least 1.1, more preferably at least 2. The ratio between $D_{FE}$ and $D_{BE}$ will generally not be more than 10.

The method of the invention comprises the step of providing an aqueous mixture comprising polycarboxylic acid and dissolved halide salt. The aqueous mixture is the mixture to be extracted with the organic liquid.

The aqueous mixture is preferably an aqueous solution, since extraction can be more easily conducted when no solid matter is present. Such a solution may be referred to as an aqueous feed solution. Nevertheless, the presence of solid matter in the aqueous mixture is possible to a certain extent, dependent on the equipment used, as will be evident to the skilled person. Thus, the aqueous mixture can also be a suspension. Examples of solid matter that can be present in such a suspension are carboxylic acid in solid form, undissolved halide salt and insoluble impurities.

The aqueous mixture comprises polycarboxylic acid, in the present specification often shortened to carboxylic acid. In one embodiment the polycarboxylic acid is a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, mandelic acid, malic acid, and tartaric acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

The carboxylic acid content present in the aqueous mixture is preferably as high as possible. In general, the carboxylic acid content is limited by the solubility of the acid in the aqueous mixture. The aqueous mixture may comprise carboxylic acid in solid form, but preferably the solid content is as low as possible as solids may create a more challenging extraction and phase separation. It is within the scope of the skilled person do determine the type of commercially available extraction equipment able to handle solids. Accordingly, the carboxylic acid content in the aqueous mixture is may be higher, but is preferably equal to or lower than the solubility of the carboxylic acid in the aqueous mixture. Preferably, more than 99 wt. % of the carboxylic acid present in the aqueous mixture is in dissolved form.

In one embodiment, the amount of acid is at least 50% of the maximum amount of acid that can be dissolved in the aqueous salt-containing mixture under extraction conditions, in particular at least 70%.

In one embodiment, the aqueous mixture has a pH of 2 or lower, typically a pH below 1, for example a pH of 0-1. It is preferred for the pH to be relatively low, to ensure that the carboxylic acid is present in the mixture in acidic form, allowing extraction.

The aqueous mixture may further comprise impurities, in particular impurities originating from a fermentation process. Such impurities may be soluble or insoluble in the aqueous mixture. Examples of dissolved impurities are sugars, proteins, and salts. Insoluble biomass (e.g. microorganisms) and insoluble salts are examples of insoluble impurities. These impurities may all be typically present in a fermentation broth. More details on how to obtain the aqueous mixture are provided below.

The aqueous mixture comprises at least 5 wt. % dissolved halide salt. Dissolved halide salt as used herein refers to halide salt in its dissolved state, i.e. in the form of solvated ions, in water. The dissolved halide salt may originate from an acidulation reaction wherein a polycarboxylate salt is reacted with a halogen acid. The dissolved halide salt may also originate from adding halide salt to an aqueous mixture to increase its dissolved halide salt concentration. Combinations are of course also possible.

As to the amount of dissolved salt, the following is remarked. The effects described above are more pronounced when larger amounts of dissolved halide salt are present in the aqueous mixture. For this reason it may be preferred to use relatively large salt concentrations. On the other hand, the presence of large amounts of salts may decrease the solubility of the acid in the mixture to a value which is so low that no meaningful extraction can be carried out. In general, a salt concentration of more than 30 wt. % is therefore not desirable. Depending on the amount and nature of the acid, and on the nature of the salt, it may be preferred for the amount of salt to be at least 8 wt. %, or at least 10 wt. %. Again, depending on the amount and nature of the acid, and on the nature of the salt, it may be preferred for the amount of salt to be at most 20 wt. %, or at most 15 wt. %. It is within the scope of the skilled person to determine the suitable salt concentration on a case-by-case basis.

The cations present in the halide salt are preferably one or more selected from the group consisting of magnesium, calcium, potassium, sodium, nickel, cobalt, iron and aluminium, and ammonium. The use of one or more cations selected from the group of magnesium, calcium, sodium, and potassium is preferred. The use of calcium and magnesium is particularly preferred, as these cations show a particularly large concentration effect. The use of magnesium may be especially preferred for this reason. While mixtures of cations may be used, for reasons of processing efficiency it is preferred for the at least 90% of the cation in the halide salt to be of a single type, according to the preferences specified above. Preferably, the cation is magnesium, as explained below.

The halide salt may be a fluoride, chloride, bromide, or iodide. The use of chloride is preferred. This selection applies in combination with the preference for the cations specified above. Specific examples of preferred salts are $MgCl_2$, $CaCl_2$, NaCl, and KCl. It was found that these salts contribute to the concentration effect of the present invention. The use of calcium and magnesium chloride is considered preferred, as they show a high concentration effect. The use of magnesium chloride may be particularly preferred, as it combines a high concentration effect with suitable possibilities for further processing, as will be discussed further below.

In one embodiment, the halide salt is capable of thermal decomposition into HCl. In this embodiment, the halide obviously is a chloride. Examples of salts capable of thermal decomposition into HCl are chloride salts selected from the group consisting of beryllium chloride, magnesium chloride, titanium chloride, vanadium chloride, chromium chloride, manganese chloride, iron chloride, cobalt chloride, nickel chloride, aluminium chloride, yttrium chloride and zirconium chloride. Such salts can be recycled using thermal decomposition as described below. Good results have been obtained using $FeCl_3$ and $MgCl_2$.

The aqueous mixture may be prepared by adding halide salt to an aqueous premixture comprising carboxylic acid. However, the aqueous mixture is preferably prepared by acidifying a carboxylate salt with an acid, thereby forming an aqueous mixture comprising carboxylic acid and an halide salt. The acidulation step is typically conducted by bringing the carboxylate salt in contact with an acidic solution. However, in some embodiments it may also be possible to contact the carboxylate salt with gaseous acid, for example in certain cases when using HCl.

Suitable carboxylate salts are generally those that are capable of forming an halide salt when acidulated, i.e. carboxylate salts of an inorganic cation. Examples of suitable carboxylate salts are magnesium carboxylate, calcium carboxylate, sodium carboxylate and potassium carboxylate. In view of the desirable recycle step using thermal decomposition, and in view of the pronounced concentration effect obtained for this compound, preferably magnesium carboxylate is used.

The carboxylate salt may be in solid and/or dissolved form. In one embodiment, the carboxylate salt is provided in solid form. In this case, the acidulation step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25 wt. %, up to, e.g. 50 wt. %, or e.g. 40 wt. %. The carboxylate salt may also be in dissolved form, typically as part of an aqueous solution. In this case, the acidulation step can be conducted by bringing the carboxylate salt in contact with an acidic solution or an acidic gas. This embodiment may be preferred for the polycarboxylic acids of the present invention.

The acidulation step may also be conducted on a mixture of carboxylic acid and carboxylate salt. Such a mixture may for example be obtained in a low pH fermentation. The mixture may for example be an aqueous suspension or solution.

The acid used in the acidulation step is typically a strong acid, such as hydrochloric acid or sulfuric acid. In view of the required presence of at least 5 wt. % of a halide salt, the use of hydrochloric acid is preferred. In such a case, an aqueous mixture is obtained comprising carboxylic acid and a chloride salt. HCl acidulation may for example be conducted by bringing the carboxylate salt in contact with an aqueous HCl solution or by bringing a carboxylate salt solution or suspension in contact with HCl gas.

When acidulation of the carboxylate salt is conducted by contacting it with an acidic solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution. Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case an acidic gas is used (e.g. HCl gas), it may be contacted by bringing it in contact with a carboxylate solution or suspension. In particular, HCl gas may be blown through the solution or suspension. In case HCl gas is used, the HCl may originate from a thermal decomposition step, as described above.

Preferably, acidulation is conducted at a temperature of 75° C. or less. At higher temperatures, it becomes uneconomical to adapt equipment to the harsh conditions of an acidic environment at high temperatures.

After acidulation, solid material may be removed from the aqueous mixture, for example by filtration. For example, in the case that the polycarboxylic acid has a low solubility in water, the carboxylic acid that precipitates during the acidification step can be filtered off, with the remaining solution containing dissolved carboxylic acid and halide salt being subjected to extraction by the process according to the invention.

The aqueous mixture may be concentrated after acidulation prior to extraction to a concentration step. The upper limit for the concentration step generally is the solubility of the halide salt or of the polycarboxylic acid, whichever precipitates first. Suitable concentrations for these compounds have been described elsewhere.

In one embodiment, a carboxylate salt is used which originates from a fermentation process. Accordingly, the method of the invention may further comprise a fermentation step to form the carboxylic acid, which fermentation process comprises the steps of fermenting a carbon source, such as a carbohydrate, by means of a micro-organism in a fermentation broth to form carboxylic acid and neutralizing at least part of the carboxylic acid by addition of a base, in particular a magnesium or calcium base, thereby obtaining a carboxylate salt.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising a carboxylate salt, biomass, and optionally further components, such as impurities like are sugars, proteins, and salts.

If so desired, the fermentation broth may be subjected to a biomass removal step, e.g., a filtration step, before further processing. This is generally preferred for improving product quality.

Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

Overall, for polycarboxylic acids one embodiment of a suitable processing sequence would be as follows:
forming a fermentation medium comprising a dissolved polycarboxylate salt, as described above,
optional removal of biomass as described above,
optional concentration step to increase the concentration of the polycarboxylate salt,
acidification, to convert the polycarboxylate salt into polycarboxylic acid, with accompanying formation of halide salt,
separation of insoluble polycarboxylic acids from the mixture to yield a liquid containing polycarboxylic acid to its solubility level and halide salt
optional concentration of the solution to increase the halide salt concentration (where necessary followed by removal of further precipitated acid), or optional addition of halide salt, to ensure the desired halide salt concentration
extraction, as described above.

In the method according to the invention, the aqueous mixture discussed above is subjected to an extraction step by contacting it with an organic liquid comprising an organic solvent selected from the group of ketones and ethers, thereby obtaining an organic carboxylic acid solution and an aqueous waste liquid comprising the halide salt. In this forward extraction, the carboxylic acid is separated from the impurities present in the aqueous mixture by dissolving it in the first organic liquid. The impurities will remain in the aqueous mixture.

Preferably, the organic liquid comprises at least 90 wt. % of the organic solvent, preferably at least 95 wt. %, more preferably at least 99 wt. %. In one embodiment, the organic liquid is the organic solvent. Typically, small amounts of water can be present in the first organic liquid, in particular when the liquid (partly) comprises recycled organic solvent from a recycle step after extraction.

The organic solvent is selected from the group of ketones and ethers. It has been found that these compounds show good properties in the process according to the invention, where they show a good concentration effect. Selection of a suitable organic solvent may contribute to establishing a high distribution ratio during forward extraction. In that case, only a relatively small amount of carboxylic acid will be lost in the aqueous waste liquid.

It is preferred to use ketones, in particular C5+ ketones, more in particular C5-C8 ketones in the present invention. C5+ stands for ketones with at least 5 carbon atoms. Mixtures may also be used. The use of C9+ ketones is less preferred, because these compounds are believed to show a lower concentration effect, and may result in more contaminants in the end product. The use of methyl-isobutyl-ketone (MIBK) has been found to be particularly attractive to obtain a good concentration effect. Additionally, the use of ketones has been found to be preferred because they are stable under process conditions, in that they do not react or decompose to a substantial extent, thus giving rise to few contaminants, and allow a stable process operation. Ethers may also be used, in particular C3-C6 ethers. It has been found, however, that they are less preferred, in particular because the use of ethers results in more solvent loss and in more contaminants in the end product. Within de ether-group, the use of methyl tert-butyl ether (MTBE) and diethyl ether (DEE) may be preferred, but less preferred than the use of ketones.

The method of the invention does not require the use of extracting agents, such as amines. In fact, the use of extracting agents in the organic solvent is generally undesirable. An extracting agent is a compound that forms a complex with the compound to be extracted (in this case carboxylic acid). However, the formation (during forward extraction) and breakage of the complex would require a relatively large amount of energy, such that the difference in temperature between forward and back extraction would need to be larger than necessary. Accordingly, the organic liquid preferably comprises no or substantially no extracting agents, in particular no or substantially no amine extracting agents. Thus, the carboxylic acid in the method of the invention is preferably extracted in its neutral acidic form and not in the form of a salt or a complex.

The organic liquid is preferably essentially free of amines, ethers, and alcohols, which means that these compounds, if present at all, are each present in an amount of less than 2 wt. %, preferably less than 1 wt. %, more preferably less than 0.5 wt. %, calculated on the weight of the organic liquid.

The ratio of organic liquid to aqueous mixture used in forward extraction is determined by the following considerations. On the one hand, if the amount of organic liquid is relatively high, the efficiency of the extraction, expressed as the percentage of acid in the aqueous mixture which is extracted into the organic liquid will be high. On the other hand, a large amount of organic liquid will have to be used, and the concentration effect will be reduced. Conversely, if the amount of organic liquid is relatively low, the concentration effect will be improved, but the extraction efficiency will be reduced.

The Distribution Ratio (DR) defined above can give guidance in this respect. In one embodiment, the amount of organic liquid used in the forward extraction may be in the range of 0.5/DR to 1.5/DR times the amount of aqueous mixture. The use of an amount of organic liquid in the range of 0.5/DR to 0.8/DR times the amount of aqueous mixture for forward extraction may be desirable for a good concentration effect. However, the yield of the extraction step may in this case be less than 99%. The use of an amount of organic liquid in the range of 1.3/DR to 1.5/DR times the amount of aqueous mixture for forward extraction may result in an extraction yield of over 99%, but typically has a less pronounced concentration effect. The use of an amount of organic liquid in the range of 0.8/DR to 1.3/DR, and in particular in the range of 1.0/DR to 1.2/DR, times the amount of aqueous mixture for forward extraction is most desirable, because both a good concentration effect and an extraction yield of over 99% can be obtained. The extraction yield as used herein refers to the weight percentage of the carboxylic acid that is extracted into the organic liquid during forward extraction.

Forward extraction is typically conducted by contacting the aqueous mixture with the first organic liquid, thereby obtaining an organic carboxylic acid solution and an aqueous waste liquid comprising the halide salt. Preferably, the extraction is a counter-current extraction, i.e. the aqueous mixture and organic liquid are contacted with each other using counter-current streams. In such a configuration, a very efficient extraction of carboxylic acid into the organic liquid can be obtained, in particular with respect to the yield.

The extraction is preferably conducted in an extraction column. In case the organic solvent used has a lower density than water (for example in case of MIBK), the organic solvent is preferably fed to the bottom of the column, while the aqueous mixture is fed at the top of the column.

Consequently, two phases will form: an upper phase comprising the organic solvent and a lower phase comprising the aqueous mixture. At the interface of the two phases, any biomass and/or other solid matter present in the aqueous mixture will accumulate. As described above, the biomass does not cause emulsification due to the presence of the salt in the aqueous mixture. By feeding the organic solvent at the bottom of the column, the organic solvent will move upwards through the aqueous mixture, thereby extracting the carboxylic acid and forming an organic carboxylic acid solution. At the bottom of the column, an aqueous waste liquid can be obtained, typically in the form of an aqueous salt solution, which solution comprises the halide salt.

Forward extraction may be conducted at a temperature of 20-100° C., preferably at a temperature of 30-80° C., for example at a temperature of 40-60° C. To reach the desirable temperature for forward extraction, the aqueous mixture and/or organic liquid may be heated prior to forward extraction. As described above, higher temperatures within the range of 20-100° C. are advantageous with respect to a decrease in solubility of the organic solvent in water. In addition, the distribution ratio may increase with increasing temperatures and/or may lead to a stronger concentration effect. In view of the possible corrosive conditions of the acidic aqueous mixture, a temperature above 60° C. may be disadvantageous. However, corrosion may for example be avoided by using plastic or glass-lined extraction equipment. The aqueous waste liquid formed in the forward extraction comprises the halide salt. The aqueous waste liquid is typically obtained in the form of an aqueous salt solution, which solution comprises the halide salt. This solution is relatively pure, since insoluble impurities typically remain at the interface of the water/organic interface during extraction.

To prevent acid loss from the system, it is preferred for the concentration of polycarboxylic acid in the waste liquid to be as low as possible. In one embodiment, the polycarboxylic acid concentration in the waste liquid is below 1 wt. %, in particular below 0.5 wt. %, more in particular below 0.1 wt. %. It has been found that extraction using the method according to the invention allows obtaining these very low acid losses. To prevent solvent loss from the system, and to prevent problems in further processing, in particular when use is made of a thermal decomposition step, it is preferred for the concentration of solvent in the waste liquid to be as low as possible. In one embodiment, the solvent concentration in the waste liquid is below 1 wt. %, in particular below 0.5 wt. %, more in particular below 0.2 wt. %, and preferably below 0.1 wt. %. It has been found that extraction using the method according to the invention allows obtaining these very low solvent losses.

It is preferred for at least 80% of the acid present in the system to be in the organic phase after the forward-extraction, in particular at least 90%, preferably at least 95%, more preferably at least 98%, still more preferably at least 99%. It is preferred for at least 90% of the halide salt present in the system to be present in the aqueous waste liquid after the forward extraction, preferably at least 95%, more preferably at least 98%, in particular at least 99%.

The organic polycarboxylic acid solution is subsequently submitted to a back extraction step. Optionally, the organic carboxylic acid solution obtained in the forward extraction is subjected to an intermediate washing step to remove any impurities present in the organic carboxylic acid solution. Such impurities are typically entrained from the aqueous mixture, for example chloride or metal ions. In such a washing step, the organic carboxylic acid solution is contacted with a washing liquid. Such a step may decrease the amount of impurities, such as chloride and/or metal ions in the end product, i.e. the aqueous carboxylic acid solution. The removal of these ions may further prevent corrosion problems. The washing liquid is typically an aqueous liquid. In one embodiment, part of the aqueous carboxylic acid solution formed as product in the back extraction is used as the washing liquid. In this embodiment, a small part, for example 0.5-5 wt. %, in particular 0.5-2 wt. %, of the product total aqueous carboxylic acid solution may be used for washing. The washing liquid may subsequently be recycled back to the aqueous mixture, where it will again be subjected to forward extraction. Care should be taken during washing not to remove too much acid from the organic liquid, as this will detrimentally affect the concentration of carboxylic acid in the final product. It is within the scope of the skilled person to determine suitable washing conditions.

The organic carboxylic acid solution formed in the forward extraction is, optionally after being washed, back extracted into an aqueous liquid, thereby obtaining an aqueous carboxylic acid solution and a second organic liquid. This step may be referred to herein as the second extraction or back extraction. The back extraction results in an aqueous carboxylic acid solution, which has a higher purity and in particular a lower salt concentration than the initial aqueous mixture. As explained above, the product aqueous carboxylic acid solution of the present invention typically has a higher concentration of carboxylic acid than the aqueous mixture.

The ratio of aqueous liquid to organic acid solution used in the back extraction is determined by the following considerations. On the one hand, if the amount of aqueous liquid is relatively high, the efficiency of the extraction, expressed as the percentage of acid in the organic acid solution which is extracted into the aqueous liquid will be high. On the other hand, a large amount of aqueous liquid will have to be used, and the concentration effect will be reduced. Conversely, if the amount of aqueous liquid is relatively low, the concentration effect will be improved, but the extraction efficiency will be reduced.

A suitable value for the ratio of aqueous liquid to organic acid solution used in that back extraction may be derived from the Distribution Ratio (DR) defined above. In one embodiment, the amount of aqueous liquid used in the back extraction is 0.5*DR to 1.5*DR times the amount of the organic carboxylic acid solution. These ratios may in particular be important with respect to the concentration effect of the present method. The use of an amount of aqueous liquid in the range of 0.5*DR to 0.8*DR times the amount of organic carboxylic acid solution for back extraction may be desirable for a good concentration effect. However, the yield of the back extraction step may in this case be less than 99% yield. The use of an amount of aqueous liquid in the range of 1.3*DR to 1.5*DR times the amount of organic carboxylic acid solution for back extraction may result in a back extraction yield of over 99%, but typically has a less pronounced concentration effect. The use of an amount of aqueous liquid in the range of 0.8*DR to 1.3*DR, and in particular in the range of 1.0*DR to 1.2*DR times the amount of organic carboxylic acid solution is most desirable, because both a good concentration effect and a back extraction yield of over 99% can be obtained. The back extraction yield as used herein refers to the weight percentage of the carboxylic acid that is extracted into the aqueous liquid during back extraction. Back extraction is typically conducted by contacting the organic carboxylic acid solution with the aqueous liquid, thereby obtaining an aqueous carboxylic acid solution and a second organic liquid. The aqueous carboxylic acid solution is the product solution. If so desired, the second organic liquid, in its entirety or in part, may be recycled to the forward extraction as first organic liquid, optionally after having been subjected to a purification step. Preferably, the extraction is a counter-current extraction. In such a configuration, a very efficient extraction of carboxylic acid into the aqueous liquid can be obtained, in particular with respect to the yield.

The extraction is preferably conducted in an extraction column. In case the organic solvent used has a lower density than water, the aqueous liquid is preferably fed at the top of the column, while the organic carboxylic acid solution is fed at the bottom of the column. Consequently, two phases will form: an upper phase comprising the organic solvent and a lower phase comprising the aqueous liquid. By feeding the aqueous liquid at the top of the column, it will pass downward through the organic carboxylic acid solution, thereby extracting the carboxylic acid and forming an aqueous carboxylic acid solution. An aqueous carboxylic acid solution can then be recovered at the bottom of the column.

It is noted that it was contemplated to evaporate the organic solvent from the organic carboxylic acid solution after forward extraction, thereby directly obtaining the carboxylic acid. However, better results were obtained when using a back extraction in accordance with the present invention. Back extraction resulted in less impurities and a more energy efficient process.

Back extraction may be conducted at a temperature of 20-100° C., preferably at a temperature of 80° C. or lower, more preferably at a temperature of 60° C. or lower. Back extraction is preferably conducted at a temperature above 0° C., preferably a temperature of at least 10° C. due to energy costs associated with cooling. Temperatures equal or close to the temperature in the forward extraction are particular preferred for back extraction. This may save energy, because less heating and/or cooling is required between the different streams in the extraction process. Accordingly, in one embodiment the back extraction is conducted at a temperature that is within 10° C., for example within 5° C. of the temperature at which forward extraction is conducted. The use of a similar temperature in forward and back extraction is herein also referred to as isothermal conditions. Forward extraction and back extraction may be conducted at about the same temperature, for example using a temperature difference between forward and back extraction of less than 5° C.

In one embodiment, the extraction into the organic liquid (forward extraction) is conducted at a lower temperature than the extraction into the aqueous liquid (back extraction). Such an extraction method is also known as a regular temperature swing extraction. The temperature during back extraction is in this case 5-45° C., for example 10-20° C. higher than the temperature in forward extraction.

In another embodiment, the extraction into the organic liquid (forward extraction) is conducted at a higher temperature than the extraction into the aqueous liquid (back extraction). Such an extraction method may be indicated as a reverse temperature swing extraction. In the reverse temperature swing extraction, the back extraction step may in this case be conducted at a temperature that is 10-50° C. or 20-30° C. lower than the temperature at which forward extraction is conducted. It has been found that operating extraction in reverse temperature swing mode may lead to an increased concentration of acid in the product.

In one embodiment in the process according to the invention the organic carboxylic acid solution is brought into thermal contact with the second organic liquid using a heat exchanger. This is advantageous when forward and back extraction are conducted at different temperatures.

The aqueous carboxylic acid solution obtained after back extraction as performed according to the present invention has a higher carboxylic acid concentration than the aqueous mixture which was fed to the forward extraction. This is also illustrated in the examples below.

The extent of the concentration effect of the method of the invention depends i.a. on the ratio of the organic liquid and aqueous mixture used in forward extraction, the ratio of the aqueous liquid and organic carboxylic acid solution used for back extraction, the temperature at which the extraction steps are conducted, the type of organic liquid used and the amount of dissolved halide salt present in the aqueous mixture. Furthermore, it is preferred to select the process conditions in such a manner that so as to obtain a high extraction yield. In this respect, it is preferred that the weight amount of organic liquid used in forward extraction is 1.0/DR to 1.2/DR times the weight amount of aqueous mixture while the weight amount of aqueous liquid used in back extraction is 1.0*DR to 1.2*DR times the weight amount of organic carboxylic acid solution. It is even more preferred that the weight amount of organic liquid used in forward extraction is 1.1/DR to 1.2/DR times the weight amount of aqueous mixture while the weight amount of aqueous liquid used in back extraction is 1.1*DR to 1.2*DR times the weight amount of organic carboxylic acid solution. These weight ratios result in a particular good concentration effect when additionally combined with a forward extraction temperature of 50-60° C. The organic liquid used is in this case preferably a ketone, more preferably MIBK. The back-extraction is in this case preferably conducted at 20-60° C., more preferably at 50-60° C.

Thus, the following combination of parameters may result in particular good concentration effect and may at the same time result in a good extraction yield:
- a forward extraction temperature of 30-60° C., in particular 50-60° C.;
- a back extraction temperature of 20-60° C.;
- a weight amount of organic liquid used in forward extraction that is 1.1/DR to 1.2/DR times the weight amount of aqueous mixture;
- a weight amount of aqueous liquid used in back extraction that is 1.1*DR to 1.2*DR times the weight amount of organic carboxylic acid solution;
- the organic liquid being a ketone, in particular a C5-C8 ketone, more in particular methylisobutylketone.

The total yield of the method of the invention depends both on the extraction yield in forward extraction and the extraction yield in back extraction. The yield of forward extraction can be increased by conducting the forward extraction with counter-current streams (see also above). Such counter-current extraction can be conducted in one or more vessels (e.g. a mixer or settler). The yield of the extraction step can be increased by increasing the size and/or the number of the vessel(s). When using more than one vessel, the vessels are connected in series with each other. In this case, the second or further vessel further extracts the aqueous liquid obtained after extraction in the previous vessel. Preferably however, forward extraction is conducted in one vessel (e.g. an extraction column) that is sufficiently large to obtain the desired high yield (typically above 99%). For example, large extraction columns with a height of 10-20 meter are known in the art. The skilled person will be able to adjust the size and/or number of the vessels to obtain a yield of 99% or more.

The yield of back extraction can be increased in the same way as described above for forward extraction. In case more than one vessel is used, the second or further vessel further extracts the organic liquid obtained after extraction in the previous vessel.

The method of the invention may further comprise the step of concentrating the product aqueous carboxylic acid solution by evaporation of water. The water evaporated in this step may be recycled by reusing it as the aqueous liquid in back extraction. It is possible for the product aqueous carboxylic acid solution to comprise a minor amount of organic solvent and residue from the extraction step, if present e.g. of the order of 0.1-3 wt. % based on the total amount of the aqueous carboxylic acid solution. Where an evaporation step is carried out, organic solvent is also typically evaporated in the concentration step, often enhanced by a stripping effect of water.

As indicated above, the second organic liquid obtained in the back extraction can be recycled by reusing it as the first organic liquid in the forward extraction.

In case the halide salt is a chloride salt (e.g. $MgCl_2$), the method of the invention preferably comprises the step of subjecting the aqueous waste liquid obtained in forward extraction to a thermal decomposition step at temperatures of at least 300° C., thereby forming a metal oxide (e.g. MgO) and HCl. In this step, the chloride salt is thermally hydrolyzed under formation of metal oxide and HCl, which compounds can be recycled in other stages in a process for carboxylic acid preparation. For example, the metal oxide may be used in a fermentation process, for example as a neutralizing agent or as a precursor thereof. The metal oxide may for this purpose be brought in contact with water to obtain a metal hydroxide (e.g. $Mg(OH)_2$) slurry. Furthermore, HCl may be used to acidify magnesium carboxylate obtained in a fermentation process. HCl is typically dissolved in water during or after thermal decomposition, thereby obtaining a HCl solution. Thus, the thermal decomposition step provides for a process wherein the waste material is recycled and wherein consequently relatively little waste is produced.

The method of the invention is preferably a continuous process. However, it may also be conducted as a batch process.

The invention will further be illustrated by the following examples, without being limited thereto or thereby.

General Procedure

The general procedure is set up to mimic a continuous extraction process. That is, the volume ratios between the extractant and the medium to be extracted are such that the concentration of the acid in the medium to be extracted is not significantly affected by the extraction.

A feed solution was prepared comprising acid and salt in the amounts stipulated in the table. The solutions were stirred overnight.

1000 g of this feed solution was mixed with approximately 100 g of methyl-isobutylketone as solvent and stirred at 20° C. for minimum of 15 minutes. The mixture was transferred to a separation funnel where phases were separated. Samples of both phases were taken for analysis. Then approximately 100 g of organic phase was mixed with 10 g of pure water and stirred for minimum of 15 min at 20° C. Subsequently the whole mixture is again transferred to the separation funnel, phases are left to separate and samples of both phases are taken. Samples were analysed on acid content.

EXAMPLE 1: EXTRACTION OF DIFFERENT TYPES OF ACIDS

Solutions containing magnesium chloride as salt and, respectively succinic acid, itaconic acid, and fumaric acid. The composition of the feed solutions is presented in table 1.1. The results are given in tables 1.2, 1.3, and 1.4. These tables also give the concentration ratio, which is the ratio between the acid concentration in the product and the acid concentration in the feed.

TABLE 1.1

| Example | Acid type | wt. % acid | wt. % $MgCl_2$ |
|---|---|---|---|
| 1.1 | succinic acid | 1.5 | 15 |
| 1.2 | itaconic acid | 1.5 | 15 |
| 1.3 | fumaric acis | 0.12 | 15 |

TABLE 1.2

| Succinic acid | |
|---|---|
| [acid] feed | 1.5 wt. % |
| [acid] aqueous fraction after back extraction | 3.1 wt. % |
| concentration ratio | 2.1 |
| $D_{FE}$ | 0.86 |
| $D_{BE}$ | 0.26 |
| $D_{FE}/D_{BE}$ | 3.3 |

TABLE 1.3

| Itaconic acid | |
|---|---|
| [acid] feed | 1.5 wt. % |
| [acid] aqueous fraction after back extraction | 2.8 wt. % |
| concentration ratio | 1.9 |
| $D_{FE}$ | 2.83 |
| $D_{BE}$ | 1.07 |
| $D_{FE}/D_{BE}$ | 2.64 |

TABLE 1.4

| Fumaric acid | |
|---|---|
| [acid] feed | 0.12 wt. % |
| [acid] aqueous fraction after back extraction | 0.21 wt. % |
| concentration ratio | 1.8 |
| $D_{FE}$ | 1.75 |
| $D_{BE}$ | 0.24 |
| $D_{FE}/D_{BE}$ | 7.29 |

EXAMPLE 2: EFFECT OF TYPE OF SALT

To investigate the effect of the nature of the salt, succinic acid was extracted from solutions containing succinic acid and different types of salts. The composition of the starting solution and the acid concentration in the products is in Table 2.1 below. From the table it can be seen that magnesium chloride shows a particularly high concentration ratio.

| | type and amount of salt in feed | [succinic acid] feed | [succinic acid] product | concentration ratio |
|---|---|---|---|---|
| 2.1 | $MgCl2$-15 wt. % | 1.5 wt. % | 3.1 wt. % | 2.1 |
| 2.3 | $CaCl2$-15 wt. % | 2.0 wt. % | 3.3 wt. % | 1.7 |
| 2.4 | NaCl-15 wt. % | 2.8 wt. % | 3.6 wt. % | 1.3 |

The invention claimed is:

1. Method for recovering polycarboxylic acid from an aqueous mixture comprising the steps of
   a) providing an aqueous mixture comprising polycarboxylic acid and from 5 to 30 wt. % dissolved chloride salt, based on the total weight of water and dissolved material in the aqueous mixture,
   b) extracting the polycarboxylic acid from the aqueous mixture into a first organic liquid comprising at least 90 wt. % of an organic solvent selected from the group consisting of C5-C8 ketones and C3-C6 ethers to obtain an organic polycarboxylic acid solution and an aqueous waste liquid comprising the chloride salt;
   c) extracting the polycarboxylic acid from the organic polycarboxylic acid solution into an aqueous liquid to obtain an aqueous polycarboxylic acid solution and a second organic liquid; and d) subjecting the chloride salt solution obtained in step b) to a thermal decomposition step to yield HCl.

2. Method according to claim 1, wherein the aqueous mixture comprises from 8 to 20 wt. % of dissolved chloride salt.

3. Method according to claim 1, wherein the organic solvent comprises at least one C5-C8 ketone.

4. Method according to claim 1, wherein the first extraction step b) is conducted at a temperature of at least 30° C.

5. Method according to claim 1, wherein the second extraction step c) is conducted at a lower temperature than the temperature at which the first extraction step b) is conducted.

6. Method according to claim 1, wherein the second extraction step c) is conducted within 10° C. of the temperature at which the forward extraction step b) is conducted.

7. Method according to claim 1, wherein the polycarboxylic acid is a di- or tri-carboxylic acid comprising at least 2, but no more than 6 carbon atoms (C2-6 carboxylic acid).

8. Method according to claim 7 wherein the polycarboxylic acid is selected from the group of succinic acid, citric acid, fumaric acid, itaconic acid, adipic acid, maleic acid, 2,5-furandicarboxylic acid, malic acid, and tartaric acid.

9. Method according to claim 1, wherein the cations present in the dissolved chloride salt are one or more selected from the group consisting of magnesium, calcium, sodium and potassium ions.

10. Method according to claim 1, wherein the organic solvent comprises substantially no extractants, said extractants being compounds which form a complex with the polycarboxylic acid to be extracted.

11. Method according to claim 1, wherein the aqueous mixture has a pH of 2 or lower.

12. Method according to claim 1, comprising
subjecting the chloride salt solution obtained in step b) to a thermal decomposition step at a temperature of at least 300° C., thereby decomposing the chloride salt to a metal oxide and HCl; and
dissolving the HCl formed in the thermal decomposition step d) in water, thereby obtaining a HCl solution.

13. Method according to claim 1, wherein said polycarboxylic acid of step a) is obtained from a fermentation process, said process comprising the steps of:
i) fermenting a carbon source by means of a microorganism in a fermentation broth to form polycarboxylic acid; and
ii) neutralizing at least part of the polycarboxylic acid by adding base to thereby obtain the corresponding carboxylate.

14. Method according to any of the previous claims, wherein the method further comprises the step of
preparing an aqueous mixture by acidifying a polycarboxylate salt with an acid, thereby obtaining a polycarboxylic acid which is partially in solid form and partially dissolved and a dissolved chloride salt,
subjecting the aqueous mixture to a separation step to separate the solid polycarboxylic acid from the aqueous medium comprising dissolved polycarboxylic acid and dissolved chloride salt, and
subjecting the aqueous mixture comprising dissolved polycarboxylic acid and dissolved chloride salt to an extraction step.

15. Method according to claim 3, wherein the organic solvent is a C5-C8 ketone.

16. Method according to claim 3, wherein the organic solvent is methyl isobutyl ketone.

17. The method according to claim 5, wherein said second extraction step is conducted at a temperature 10 to 50° C. lower than the temperature at which the first extraction is conducted.

18. The method according to claim 14, wherein the polycarboxylate salt is acidified with an aqueous HCl solution.

19. The method according to claim 14, wherein the polycarboxylate salt is acidified with gaseous HCl.

20. The method according to claim 1, wherein the first organic liquid comprises no amine extractants, said amine extractants being amine compounds which form a complex with the carboxylic acid to be extracted.

21. The method according to claim 1, wherein
the chloride salt of step a) is $MgCl_2$, and
step d) comprises subjecting the magnesium chloride salt solution derived in step b) to a thermal decomposition step at a temperature of at least 300° C. to decompose the chloride salt to magnesium oxide and HCl.

22. The method according to claim 21, further comprising recycling the magnesium oxide in a fermentation process as a neutralizing agent.

23. The method according to claim 21, further comprising:
bringing magnesium oxide into contact with water to form magnesium hydroxide; and
recycling said magnesium hydroxide in a fermentation process as a neutralizing agent.

24. The method according to claim 21, wherein said HCl is dissolved in water, to form an HCl solution.

25. The method according to claim 21, wherein said HCl is used to acidify magnesium carboxylate obtained in a fermentation process.

26. Method according to claim 1, further comprising
subjecting the chloride salt solution obtained in step b) to a thermal decomposition step at a temperature of at least 300° C., thereby decomposing the chloride salt to a metal oxide and HCl;
dissolving the HCl formed in the thermal decomposition step d) in water, thereby obtaining a HCl solution; and,
recycling the metal oxide in a fermentation process as a neutralizing agent or precursor thereof.

27. Method according to claim 1, wherein the method further comprises the steps of
preparing an aqueous mixture by acidifying a polycarboxylate salt with an acid, thereby obtaining a polycarboxylic acid which is partially in solid form and partially dissolved and a dissolved chloride salt,
subjecting the aqueous mixture to a separation step to separate the solid polycarboxylic acid from the aqueous medium comprising dissolved polycarboxylic acid and dissolved chloride salt, and
subjecting the aqueous mixture comprising dissolved polycarboxylic acid and dissolved chloride salt to an extraction step, with intermittent concentration or adjustment of the chloride salt concentration.

* * * * *